(12) United States Patent
Takahashi et al.

(10) Patent No.: US 12,207,788 B2
(45) Date of Patent: Jan. 28, 2025

(54) ENDOSCOPE APPARATUS, OPERATING METHOD OF ENDOSCOPE APPARATUS, AND INFORMATION STORAGE MEDIUM

(71) Applicant: OLYMPUS CORPORATION, Tokyo (JP)

(72) Inventors: Jumpei Takahashi, Halstenbek (DE); Masashi Hirota, Hachioji (JP); Yasunori Morita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 654 days.

(21) Appl. No.: 17/469,093

(22) Filed: Sep. 8, 2021

(65) Prior Publication Data

US 2021/0401268 A1 Dec. 30, 2021

Related U.S. Application Data

(63) Continuation of application No. PCT/JP2019/011330, filed on Mar. 19, 2019.

(51) Int. Cl.
*A61B 1/00* (2006.01)
*A61B 1/06* (2006.01)

(52) U.S. Cl.
CPC .... *A61B 1/000094* (2022.02); *A61B 1/00006* (2013.01); *A61B 1/00045* (2013.01); *A61B 1/0661* (2013.01)

(58) Field of Classification Search
CPC .......... A61B 1/00006; A61B 1/000094; A61B 1/00045; A61B 1/0638; A61B 1/0661
(Continued)

(56) References Cited

U.S. PATENT DOCUMENTS

2012/0257029 A1* 10/2012 Igarashi ................. A61B 1/044
348/E9.002
2012/0327205 A1 12/2012 Takahashi
(Continued)

FOREIGN PATENT DOCUMENTS

CN 102695446 A 9/2012
JP 2011-218090 A 11/2011
(Continued)

OTHER PUBLICATIONS

Chinese Office Action dated Dec. 26, 2023 received in 201980093833.8.
(Continued)

*Primary Examiner* — Behrooz M Senfi
(74) *Attorney, Agent, or Firm* — Scully, Scott, Murphy & Presser, P.C.

(57) ABSTRACT

An endoscope apparatus includes a processor. An image signal includes a first image signal corresponding to first light and a second image signal corresponding to second light. The processor determines at least one of whether or not a submucosa region or a bleeding region is included in an image based on the image signal. In a case where the submucosa region is included, the processor performs conversion processing that increases a combination ratio of the second image signal to the first image signal in an image region including the submucosa region, and allocates a combined image signal to a G-channel. In a case where the bleeding region is included, the processor performs conversion processing that increases a combination ratio of the first image signal to the second image signal in an image region including the bleeding region, and allocates the combined image signal to the G-channel.

12 Claims, 10 Drawing Sheets

(58) Field of Classification Search
USPC .......................................................... 348/68
See application file for complete search history.

(56) References Cited

U.S. PATENT DOCUMENTS

| | | | | |
|---|---|---|---|---|
| 2013/0293693 | A1* | 11/2013 | Igarashi | .................... G06T 5/92 |
| | | | | 348/70 |
| 2013/0324797 | A1 | 12/2013 | Igarashi et al. | |
| 2013/0329027 | A1 | 12/2013 | Igarashi | |
| 2016/0089010 | A1* | 3/2016 | Aoyama | .............. A61B 1/0005 |
| | | | | 348/70 |
| 2017/0027428 | A1* | 2/2017 | Igarashi | ............... A61B 1/0655 |
| 2018/0077399 | A1* | 3/2018 | Hirota | ...................... H04N 9/76 |
| 2019/0159687 | A1 | 5/2019 | Kubo | |

FOREIGN PATENT DOCUMENTS

| | | | | | |
|---|---|---|---|---|---|
| JP | | 2017060888 A | * | 3/2017 | ......... A61B 1/00009 |
| WO | | 2012/081297 A1 | | 6/2012 | |
| WO | | 2013/145407 A1 | | 10/2013 | |
| WO | | 2013/145408 A1 | | 10/2013 | |
| WO | | WO-2018083888 A1 | * | 5/2018 | ............... A61B 1/00 |

OTHER PUBLICATIONS

International Search Report dated Jun. 11, 2019 received in PCT/JP2019/011330.
Fujimoto, At., et al., "Possibilities for Dual Red Imaging Endoscopic Therapy" Endoscopia Digestiva., Dual Red Imaging, 2016, vol. 28, No. 3, pp. 480-483, ISSN: 0915-3217.

\* cited by examiner

ENDOSCOPE APPARATUS, OPERATING METHOD OF ENDOSCOPE APPARATUS, AND INFORMATION STORAGE MEDIUM

CROSS REFERENCE TO RELATED APPLICATION

This application is a continuation of International Patent Application No. PCT/JP2019/011330, having an international filing date of Mar. 19, 2019, which designated the United States, the entirety of which is incorporated herein by reference.

BACKGROUND

Endoscopic submucosal dissection (ESD) for dissecting early cancer using an endoscope has been performed. In the ESD, a boundary between a muscle layer and a submucosa is visually recognized and the submucosa is incised, and thereby the early cancer on a mucus membrane is resected. For example, International Publication No. 2013/145407 discloses that in a case where bleeding occurs at the time of resecting a mucous membrane in the ESD, using dual red imaging (DRI) observation facilitates visual recognition of a bleeding point. The DRI observation is an observation method using illumination light including amber light and red light.

SUMMARY

According to one aspect of the disclosure, there is provided an endoscope apparatus, comprising:
a processor including hardware,
the processor being configured to be connectable to a light source device that sequentially or simultaneously emits at least first light and second light as illumination light and an imaging device that outputs an image signal, generate a display image based on the image signal, and output the display image to a display device,
the first light being narrowband light with a peak wavelength between a wavelength at which a hemoglobin absorption coefficient becomes a smallest value and a wavelength at which the hemoglobin absorption coefficient becomes a first maximum value on a short wavelength side of the wavelength at which the hemoglobin absorption coefficient becomes the smallest value,
the second light being light belonging to a blue region or a green region,
the image signal including a first image signal corresponding to the first light and a second image signal corresponding to the second light,
the processor determining at least one of whether or not a submucosa region or a bleeding region is included in an image as a specified object based on the image signal,
in a case where the submucosa, region is included, the processor performing conversion processing that increases a combination ratio of the second image signal to the first image signal in an image region including the submucosa region, allocating a combined image signal to a G-channel to perform highlighting processing of the specified object, and outputting an image after the highlighting processing as the display image, and
in a case where the bleeding region is included, the processor performing conversion processing that increases a combination ratio of the first image signal to the second image signal in an image region including the bleeding region, and allocating the combined image signal to the G-channel to perform highlighting processing of the specified object, and outputting an image after the highlighting processing as the display image.

According to another aspect of the disclosure, there is provided an operation method of an endoscope apparatus, comprising:
sequentially or simultaneously emitting at least first light and second light as illumination light, the first light being narrowband light with a peak wavelength between a wavelength at which a hemoglobin absorption coefficient becomes a smallest value and a wavelength at which the hemoglobin absorption coefficient becomes a first maximum value on a short wavelength side of the wavelength at which the hemoglobin absorption coefficient becomes the smallest value, the second light being light belonging to a blue region or a green region;
capturing an image using return light from an object irradiated with the illumination light to acquire an image signal including a first image signal corresponding to the first light and a second image signal corresponding to the second light;
determining at least one of whether or not a submucosa region or a bleeding region is included in an image as a specified object based on the image signal;
in a case where the submucosa region is included as the specified object, performing conversion processing that increases a combination ratio of the second image signal to the first image signal in an image region including the submucosa region, allocating a combined image signal to a G-channel to perform highlighting processing of the specified object, and outputting an image after the highlighting processing as a display image, and
in a case where the bleeding region is included as the specified object, performing conversion processing that increases a combination ratio of the first image signal to the second image signal in an image region including the bleeding region, allocating the combined image signal to the G-channel to perform highlighting processing of the specified object, and outputting an image after the highlighting processing as the display image.

According to another aspect of the disclosure, there is provided a non-transitory information storage medium that stores a program causing a computer to execute a method, the method comprising:
sequentially or simultaneously emitting at least first light and second light as illumination light, the first light being narrowband light with a peak wavelength between a wavelength at which a hemoglobin absorption coefficient becomes a smallest value and a wavelength at which the hemoglobin absorption coefficient becomes a first maximum value on a short wavelength side of the wavelength at which the hemoglobin absorption coefficient becomes the smallest value, the second light being light belonging to a blue region or a green region;
capturing an image using return light from an object irradiated with the illumination light to acquire an image signal including a first image signal corresponding to the first light and a second image signal corresponding to the second light;

determining at least one of whether or not a submucosa region or a bleeding region is included in an image as a specified object based on the image signal;

in a case where the submucosa region is included as the specified object, performing conversion processing that increases a combination ratio of the second image signal to the first image signal in an image region including the submucosa region, allocating a combined image signal to a G-channel to perform highlighting processing of the specified object, and outputting an image after the highlighting processing as a display image, and in a case where the bleeding region is included as the specified object, performing conversion processing that increases a combination ratio of the first image signal to the second image signal in an image region including the bleeding region, allocating the combined image signal to the G-channel to perform highlighting processing of the specified object, and outputting an image after the highlighting processing to a display device as the display image.

DESCRIPTION OF EXEMPLARY EMBODIMENTS

Figure 1:
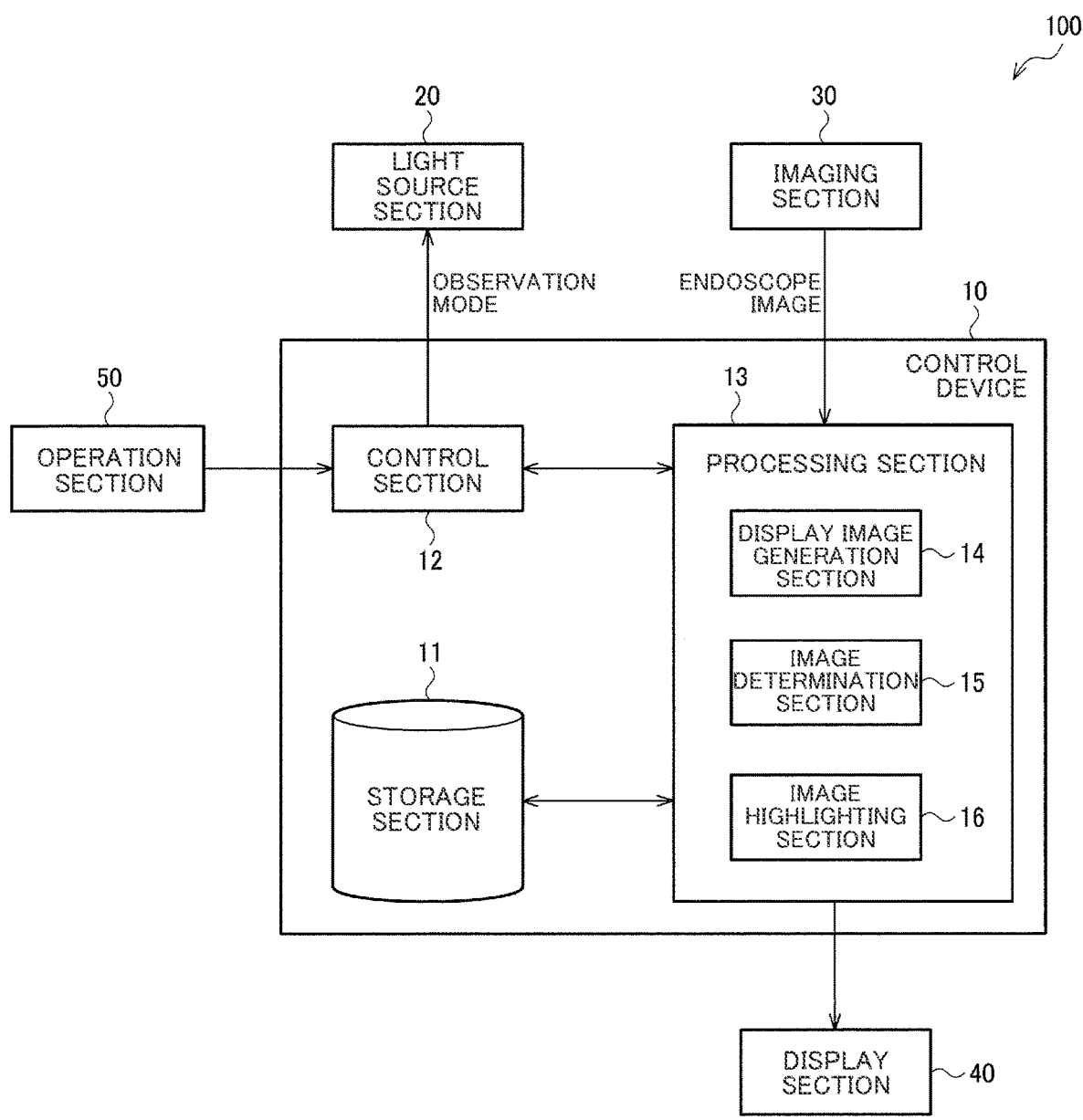
FIG. 1 illustrates a configuration example of an endoscope apparatus in accordance with the present embodiment.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Endoscope Apparatus

FIG. 1 is a diagram illustrating configuration example of an endoscope apparatus 100 in accordance with the present embodiment. The endoscope apparatus 100 includes a control device 10, a light source section 20, an imaging section 30, a display section 40, and an operation section 50. For example, a flexible scope used for a lower digestive tract can be assumed as the endoscope apparatus, but the endoscope apparatus is not limited thereto and may be a flexible scope used for an upper digestive tract, or a rigid scope used for surgery or the like.

The imaging section 30 is a device that is arranged at a distal end of a scope and that captures an object image. The imaging section 30 includes an objective lens that forms an object image, and an image sensor that captures the formed object image. The image sensor outputs an image signal to the control device 10. The image sensor may be a monochrome image sensor, or a color image sensor provided with a Bayer's primary color filter or a complementary color filter.

The endoscope apparatus 100 has a white light imaging (WLI) mode for displaying a white light image, and a dual red imaging (DPI) mode for displaying a DRI image. For example, the WLI mode or the DRI mode is set based on input information from the operation section 50.

Figure 2:
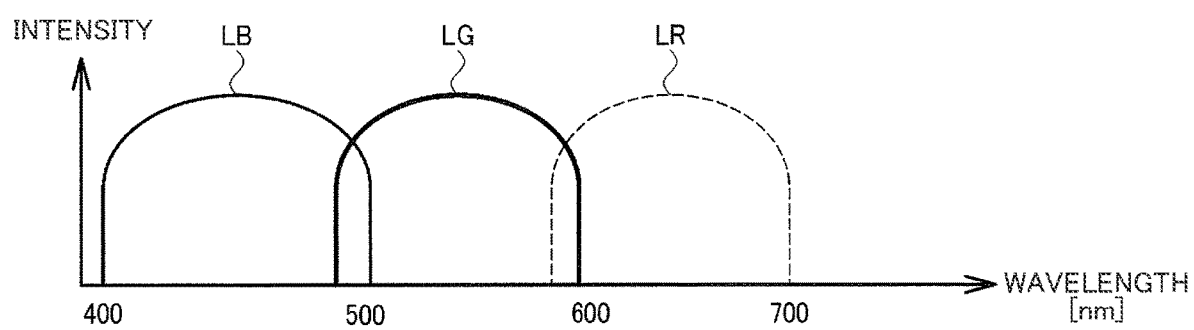
FIG. 2 illustrates an example of spectral characteristics of illumination light in a white light imaging (WLI) mode.
Figure 3:
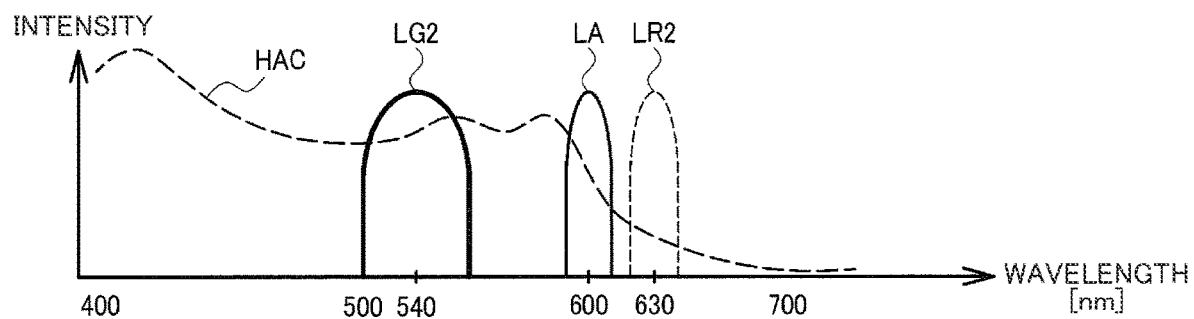
FIG. 3 illustrates an example of spectral characteristics of illumination light in a dual red imaging (DRI) mode.

The light source section 20 is a device that emits illumination light. FIG. 2 illustrates an example of spectral characteristics of illumination light in the WLI mode. FIG. 3 illustrates an example of spectral characteristics of illumination light in the DRI mode.

As illustrated in FIG. 2, the light source section 20 emits blue light LB, green light LG, and red light LR, in the WLI mode. The blue light LB is light belonging to a blue region when visible light is divided into three primary colors, and a wavelength band of the blue light LB ranges from 450 to 500 nm, for example. The green light LG is light belonging to a green region when visible light is divided into the three primary colors, and a wavelength band of the green light LG ranges from 500 to 570 nm, for example. The red light LR is light belonging to a red region when visible light is divided into the three primary colors, and a wavelength band of the red light LR ranges from 570 to 700 nm, for example.

As illustrated in FIG. 3, in the DRI mode, the light source section 20 emits green light LG2 for DRI, amber narrowband light LA, and red narrowband light LR2. Note that LG2, LA, and LR2 are hereinafter also simply referred to as green light, amber light, and red light, respectively. The green light LG2 is light belonging to the green region, and has a wavelength band that is narrower than that of the green light LG in the WLI mode. A peak wavelength of the green light LG2 is, for example, 540 nm. The amber light LA is narrowband light with a peak wavelength of 600 nm. The red light LR2 is narrowband light with a peak wavelength of 630 nm. The narrowband light is light that has a band narrower than that of each color region when a wavelength band of visible light is divided into the three primary colors. A band width of the narrowband light is, for example, several dozen nanometers.

Note that the spectral characteristics illustrated in FIGS. 2 and 3 are examples, and the spectral characteristics of illumination light are not limited thereto. For example, the LG2 is only required to have a wavelength band having a large hemoglobin absorption coefficient HAC and thereby belong to the blue region or the green region.

In addition, the peak wavelength of the amber light LA is only required to belong to a predetermined wavelength range in which the hemoglobin absorption coefficient HAC steeply changes in the red region. That is, the peak wavelength of the amber light LA is only required to be between around 730 nm at which the hemoglobin absorption coefficient HAC becomes a minimum value and 576 nm at which the hemoglobin absorption coefficient HAC becomes a first maximum value on a shorter wavelength side from the minimum value. More preferably, the peak wavelength of the amber light LA is only required to belong to a range from 585 nm to 615 nm.

In addition, the peak wavelength of the red light LR2 is only required to belong to a wavelength range in which the hemoglobin absorption coefficient HAC is small. Specifically, the peak wavelength of the red light LR2 is only required to belong to a range from 610 nm to 730 nm.

The light source section 20 includes, for example, first to sixth light emitting elements that emit the LB, the LG, the LR, the LG2, the LA, and the LR2, respectively. Light emitting elements corresponding to each mode, out of the first to sixth light emitting elements, emit corresponding light, and the light source section 20 thereby emits illumination light in each mode. The light emitting element is, for example, a light emitting diode (LED) or a laser diode (LD). Alternatively, the light source section 20 may include a white light source such as a xenon lamp, and first to sixth optical filters, through which the LB, the LG, the LR, the LG2, the LA, and the LR2 pass, respectively. An optical filter corresponding to each mode, out of the first to sixth optical filters, is inserted into an optical path, and the light source section 20 thereby emits illumination light in each mode. The illumination light is guided to the distal end of the scope by an optical fiber or the like, and the guided illumination light is diffused by an illumination lens, thereby emitting to an object. The illumination lens is arranged at the distal end of the scope.

The light source section 20 sequentially or simultaneously emits illumination light in a plurality of colors described above. First, a description is given of a case of using the monochrome image sensor. In the WLI mode, the light source section 20 sequentially emits the LB, the LG, and the LR at first to third timings, respectively, and the imaging section 30 captures images at the respective timings. In the DRI mode, the light source section 20 sequentially emits the LG2, the LA, and the LR2 at first to third timings, respectively, and the imaging section 30 captures images at the respective timings. Subsequently, a description is given of a case of using the color image sensor. In the WLI mode, the light source section 20 simultaneously emits the LB, the LG, and the LR, and the imaging section 30 captures images at this light emission timing. In the DRI mode, the light source section 20 emits the LG2 and the LR2 at the first timing, and emits the LA at the second timing. Alternatively, the light source section 20 emits the LG2 and the LA at the first timing, and emits the LR2 at the second timing. The imaging section 30 captures images at the respective timings.

Note that highlighting processing in the WLI mode uses an image captured with the amber light LA, as described later. In this case, in the WLI mode, the light source section 20 sequentially or simultaneously emits the LB, the LG, the LA, and the LR. In addition, highlighting processing in the DRI mode may use an image captured with the green light LG. In this case, in the DRI mode, the light source section 20 sequentially or simultaneously emits the LG, the LG2, the LA, and the LR2.

The control device 10 performs control of each section of the endoscope apparatus 100, and performs various kinds of signal processing such as image processing. The control device 10 is also referred to as a main section or a processor section of the endoscope apparatus 100. The control device 10 includes a storage section 11, a control section 12, and a processing section 13.

The storage section 11 stores operation setting information of the endoscope apparatus 100, records an image or a movie, or functions as a working memory of the processing section 13. The storage section 11 can include a volatile storage device and a non-volatile storage device, and includes, for example, a semiconductor memory, a hard disk drive, an optical disk drive, or the like.

The control section 12 controls each section of the endoscope apparatus 100. For example, the control section 12 sets the WLI mode or the DRI mode based on information input by a user via the operation section. 50, and outputs a corresponding mode setting signal to the light source section 20 and the processing section 13. The light source section 20 and the processing section 13 execute an operation in each mode based on the mode setting signal.

The processing section 13 performs various kinds of signal processing such as image processing. The processing section 13 includes a display image generation section 14, an image determination section 15, and an image highlighting section 16. For example, the display image generation section 14, the image determination section 15, and the image highlighting section 16 may be configured by individual circuits, or the processing section 13 may be configured by an integrated circuit. Alternatively, the processing section 13 may be implemented by a processor such as a central processing unit (CPU), as described later.

The display image generation section 14 generates a display image based on an image signal input from the imaging section 30. In the WLI mode, the display image generation section 14 generates a white light image as the display image. That is, an image signal generated by the red light LR is allocated to an R-channel of the display image, an image signal generated by the green light LG is allocated to a G-channel of the display image, and an image signal generated by the blue light LB is allocated to a B-channel of the display image. In the DRI mode, the display image generation section 14 generates the DRI image as the display image. That is, an image signal generated by the red light LR2 is allocated to the R-channel of the display image, an image signal generated by the amber light LA is allocated to the G-channel of the display image, and an image signal generated by the green light LG2 is allocated to the B-channel of the display image.

The display image generation section 14 performs image processing, such as interpolation processing, white light balance processing, and gamma conversion processing, in generation of the display image described above. For example, in a case where images in a plurality of colors are sequentially captured, the display image generation section 14 combines these images to generate a color image. In a case where images are captured by the color image sensor, the display image generation section 14 performs interpolation processing on the images to generate a color image.

The image determination section 15 determines a region in which a specified object is reflected in an image. The image determination section 15 may determine the region based on an image signal input from the imaging section 30, or based on the display image generated by the display image generation section 14. Details of a determination method will be described later. The image determination section 15 outputs information of the region, in which the specified object is determined to be reflected, to the image highlighting section 16. The information of the region is, for example, information indicating a position of a pixel belonging to the region, or information indicating a position and shape of the region.

The image highlighting section 16 performs highlighting processing on the region, in which the specified object is determined to be reflected. The image highlighting section 16 performs highlighting processing on the display image generated by the display image generation section 14, and outputs the processed display image to the display section 40. Details of the highlighting processing will be described later. In a case where no specified object is determined to be reflected in the image, the display image generated by the display image generation section 14 is output to the display section 40.

The display section 40 displays the display image input from the image highlighting section 16 or the display image generation section 14. The display section 40 is, for example, a display device, such as a liquid crystal display, an organic electroluminescence (EL) display, or the like.

The operation section 50 is a device for the user to operate the endoscope apparatus 100. The operation section 50 can include, for example, a button, a dial, a lever, a foot switch, a touch panel, and the like. The operation section 50 is arranged in the scope, the control device 10, or the display section 40.

2. Details of Operations and Processing

Details of operations and processing of the endoscope apparatus 100 is described below. First, a description is given of endoscopic submucosal dissection (ESD) as an example of treatment to which the endoscope apparatus 100 of the present embodiment is applicable. Note that treatment to which the endoscope apparatus 100 of the present embodiment is applied is not limited to the ESD, and the endoscope apparatus 100 of the present embodiment is applicable to various kinds of treatment. That is, the endoscope apparatus 100 of the present embodiment is applicable to a case in which, when a plurality of biological tissues needs to be visually recognized or identified in the treatment, the plurality of biological tissues is difficult to be visually recognized or identified because the plurality of biological tissues is not separated on a hue plane.

Figure 4:
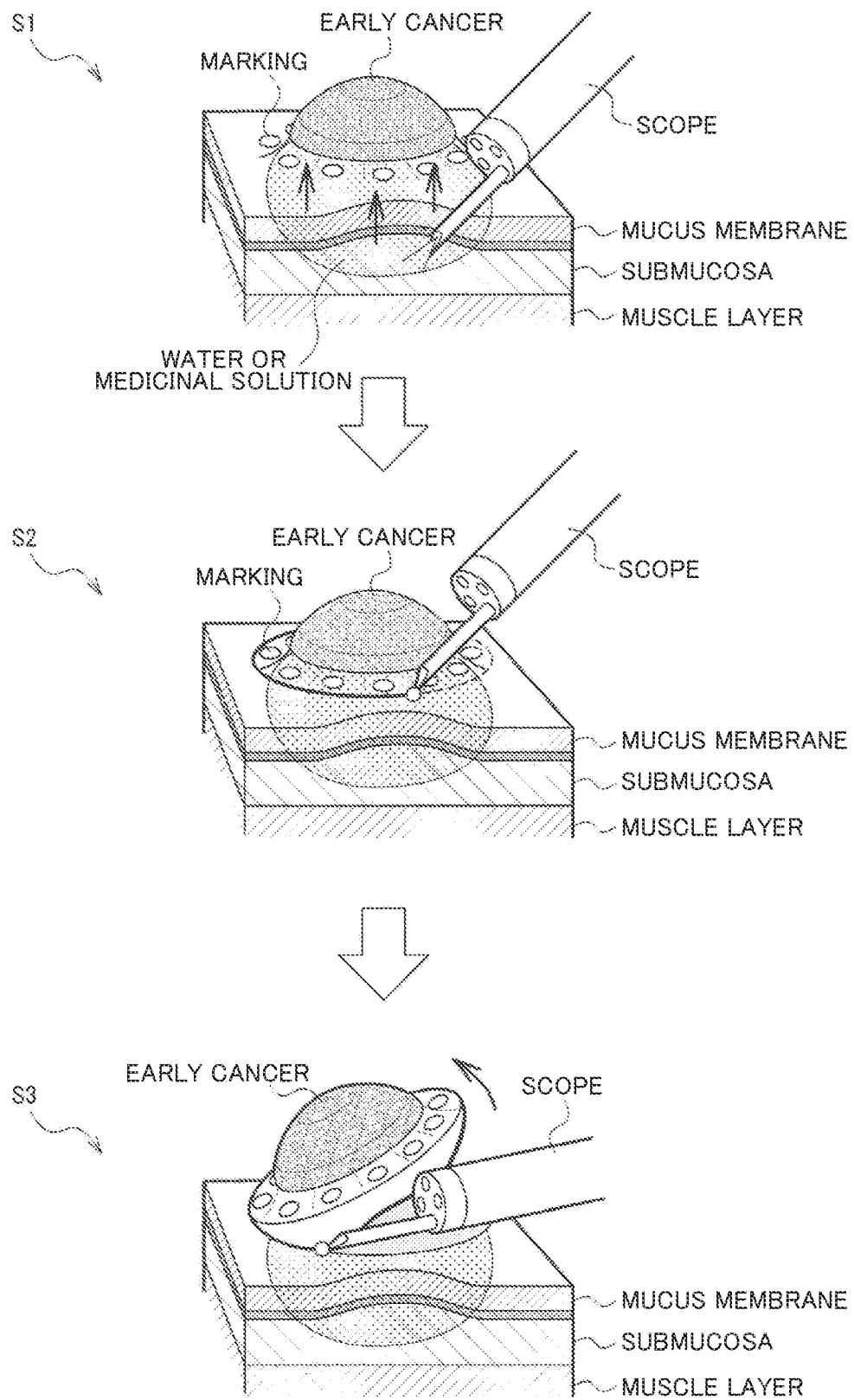
FIG. 4 is a diagram for explaining a procedure of endoscopic submucosal dissection (ESD).

FIG. 4 is a diagram for explaining a procedure of the ESD. As illustrated in FIG. 4, there is a submucosa below a mucous membrane, and there is a muscle layer further below the submucosa. Early cancer exits on the mucous membrane.

As indicated in S1, marking serving as a landmark for a resection range is added around the early cancer by an electrosurgical knife or the like. Subsequently, water or a medicinal solution is injected into the submucosa below the resection range, and the resection range is thereby lifted upward. The medical solution is, for example, indigocarmine, which is a blue dye. As indicated in S2, the mucous membrane is incised along the marking by the electrosurgical knife or the like. As indicated in S3, the submucosa is incised, and the resection range is thereby removed. Since the early cancer locally exits on the mucous membrane, the submucosa is incised, and the early cancer is thereby resected. At this time, the submucosa is incised while a boundary between the muscle layer and the submucosa is identified so that the muscle layer is not incised.

Figure 5:
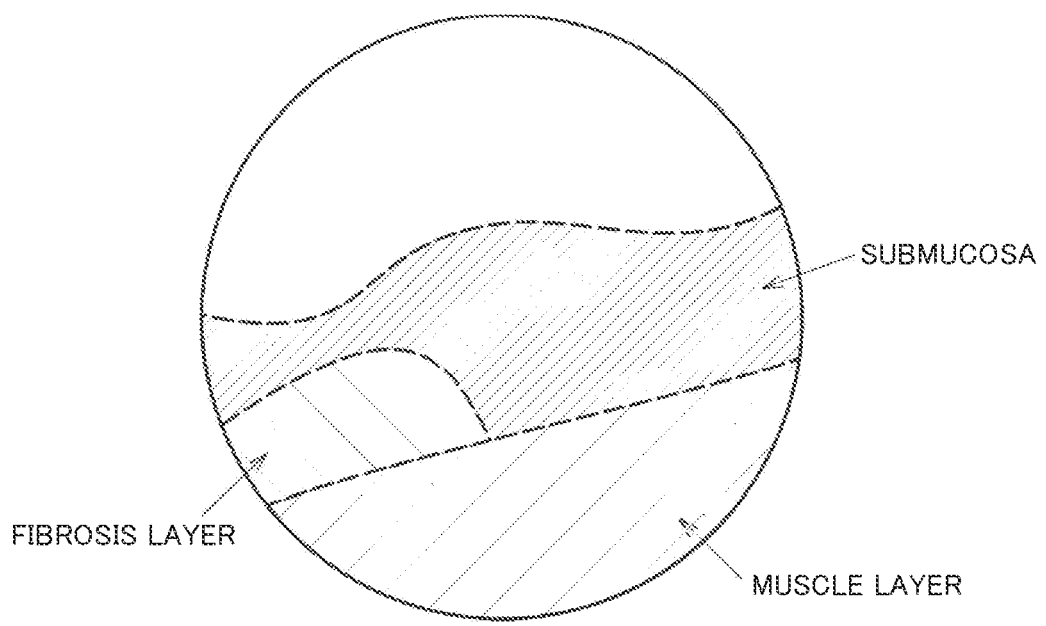
FIG. 5 illustrates an example of an endoscope image at the time of incising a submucosa in the ESD.

FIG. 5 illustrates an example of an endoscope image when incising the submucosa in the ESD. As illustrated in FIG. 5, there is a case where fibrosis occurs in part of the submucosa. The submucosa in which fibrosis occurs is referred to as a fibrosis layer. In this case, a boundary between the fibrosis layer and the muscle layer needs to be visually recognized.

In the WLI mode, the muscle layer appears to have, for example, a reddish color such as pink, and have a whitish color as compared with a color of the fibrosis layer and that of the submucosa. Specifically, as illustrated in a left drawing of FIG. 9, the color of the fibrosis layer is distributed near an origin on a CrCb plane, and the color of the muscle layer has chroma higher than that of the fibrosis layer on a fourth quadrant side. That is, in the WLI mode, the fibrosis layer and the muscle layer are separated from each other on the CrCb plane. Additionally, in the WLI mode, a fibrous structure of the fibrosis layer can be visually recognized. Hence, in the WLI mode, the muscle layer and the fibrosis layer can be identified by colors or structural information.

In contrast, in the DRI mode, the muscle layer and the fibrosis layer appear to have similar hues. Specifically, as illustrated in a left drawing of FIG. 11, each of the colors of the muscle layer and the fibrosis layer is distributed near the origin on the CrCb plane. In the DRI mode, while an image captured with the amber light is input to the G-channel of the display image, the amber light has low sensitivity to hemoglobin as compared with that of the green light. Hence, it is considered hard to cause a difference in hue between the muscle layer and the fibrosis layer.

As described above, it is preferable to use the WLI mode in terms of identifying the fibrosis layer and the muscle layer. Meanwhile, there is a case where bleeding occurs at the time of incising the submucosa or the fibrosis layer. In this case, a bleeding point is visually recognized while blood is washed away by delivery of water, and then treatment such as bleeding stopping treatment is performed. While a puddle of blood where blood is accumulated in a recessed portion is in a mixed state of blood and water by the delivery of water, it is preferable that the bleeding point can be visually recognized from the puddle of blood.

With high sensitivity to hemoglobin in the WLI mode, a region in which blood is reflected is easily saturated in red. Although a hemoglobin concentration is high around the bleeding point in the puddle of blood, the puddle of blood is easily saturated in red in the WLI mode, and thus variations in concentration of hemoglobin are hard to be visually recognized. Specifically, as illustrated in the left drawing of FIG. 9, on the CrCb plane, each of chroma in the puddle of blood in which water and blood is mixed and chroma in the bleeding point is high, and there is no difference in hue between the puddle of blood and the bleeding point.

In the DRI mode, on the other hand, the amber light having a lower hemoglobin absorption coefficient HAC than that of the green light or the like is used, so that sensitivity to hemoglobin is lower than the sensitivity in the WLI mode. This facilitates visual recognition of variations in concentration of hemoglobin. Specifically, as illustrated in the left drawing of FIG. 11, the chroma in the puddle of blood is lower than the chroma in the bleeding point and the bleeding point appears to be in darker orange.

As described above, it is preferable to use the DRI male in terms of visually recognizing the bleeding point. Since it is preferable to use the WLI mode in terms of identifying the fibrosis layer and the muscle layer as described above, there is a problem that it is difficult to provide an image that satisfies both of visual recognition of the bleeding point and identification of the fibrosis layer and the muscle layer in the conventional WLI mode and DRI mode.

A description is now given of processing of determining the specified object and processing of highlighting the specified object in accordance with the present embodiment.

Figure 6:
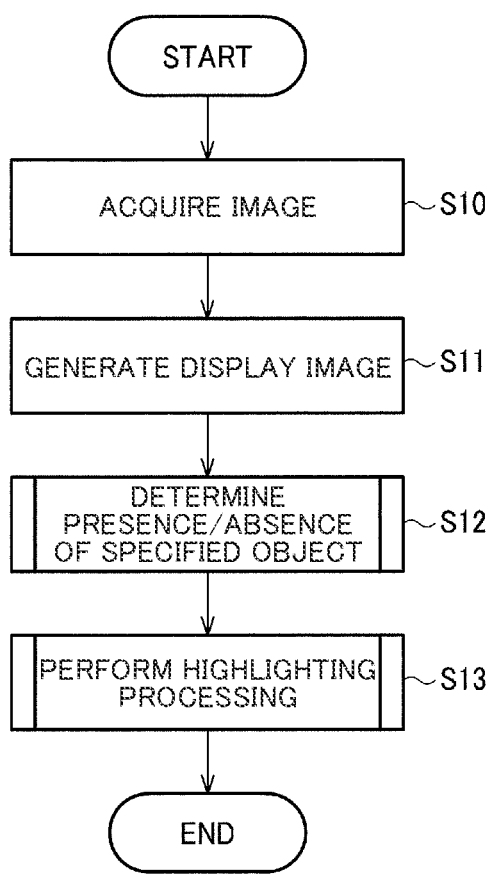
FIG. 6 is a flowchart describing a procedure of processing performed by the endoscope apparatus.

FIG. 6 is a flowchart describing a procedure of processing performed by the endoscope apparatus 100. In step S10, the light source section 20 emits illumination light and the imaging section 30 captures an image simultaneously, and an object image is thereby taken. Subsequently, in step S11, the display image generation section 14 generates a display image from an image signal input from the imaging section 30. Subsequently, in step S12, the image determination section 15 determines whether a specified object exits in the display image. Specifically, the image determination section 15 determines a region in which the specified object is reflected in the display image. Subsequently, in step S13, the image highlighting section 16 performs highlighting processing on the region in which the specified object is determined to be reflected in the display image. Steps S10 to S13 described above are performed with respect to each frame image of a movie, and the movie after subjected to the highlighting processing is displayed on the display section 40.

In steps S12 and S13, processing is different between the WLI mode and the DRI mode. Details of processing in each step are described below.

Figure 7:
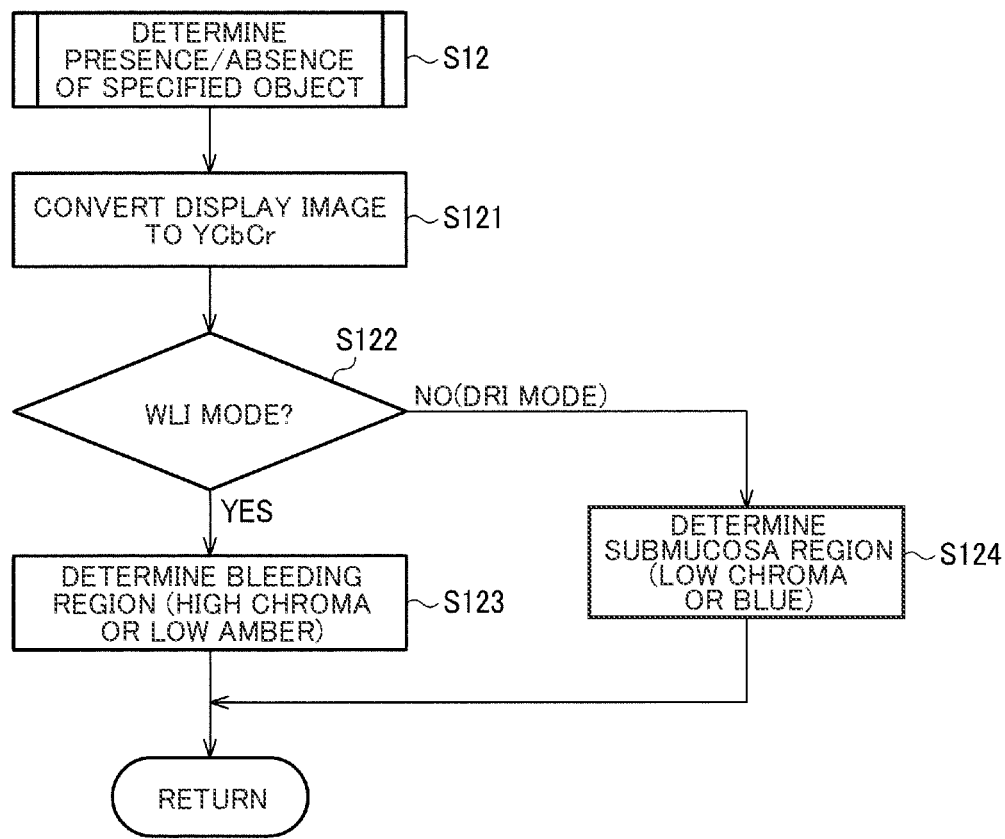
FIG. 7 is a flowchart describing a detailed procedure at the time of determining whether or not a specified object exits in a display image.

FIG. 7 is a flowchart describing a detailed procedure in step S12. In step S121, the image determination section 15 converts the display image to a YCrCb image. That is, the image determination section 15 converts an RGB value in each pixel of the display image to a YCrCb value. Subsequently, in step S122, the image determination section 15 determines whether or not a mode is the WLI mode. That is, the image determination section 15 determines the mode based on a mode setting signal input from the control section 12.

In a case of determining that the mode is the WLI mode in step S122, the image determination section 15 determines a bleeding region in the display image based on the YCrCb value in step S123. In the WLI mode, the bleeding region corresponds to the specified object. The image determination section 15 determines that a region having a high hemoglobin concentration in the object reflected in the display image is the bleeding region. Specifically, the image determination section 15 determines that a region in which a hue belongs to a predetermined hue range and chroma is higher than a first predetermined value is the bleeding region. The hue is a value in an angular direction centering on the origin on the CrCb plane, and the chroma is a value in a distance direction centering on the origin on the CrCb plane. The predetermined hue range is a hue range corresponding to red, and is, for example, a fourth quadrant of the CrCb plane.

In a case of determining that the mode is not the WLI mode, that is, the mode is the DRI mode, in step S122, the image determination section 15 determines that a submucosa region in the display image based on the YCrCb value in step S124. In the DRI mode, the submucosa region corresponds to the specified object. The image determination section 15 determines that a region having a low hemoglobin concentration in the object reflected in the display image is the submucosa region. The submucosa region determined herein includes the muscle layer and the fibrosis layer. Specifically, the image determination section 15 determines a region in which chroma is lower than a second predetermined value is the submucosa region. The second predetermined value may be different from the first predetermined value.

When step S123 or step S124 ends, step S12 ends, and step S13 is executed. Note that various modifications can be made to step S123 or step S124, and these modifications will be described later.

Figure 8:
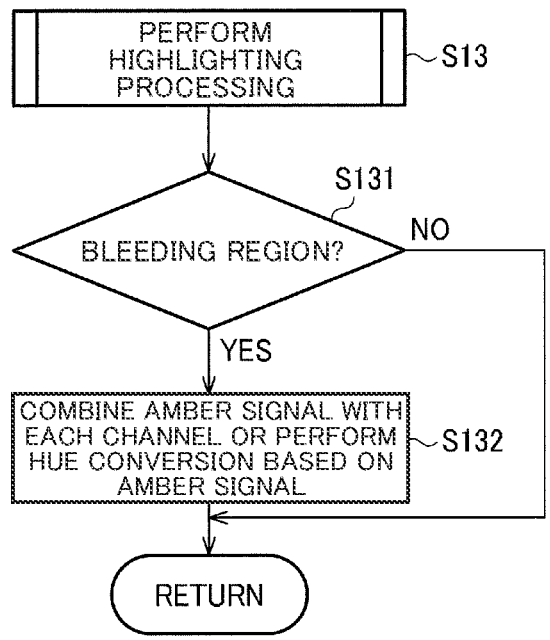
FIG. 8 is a flowchart describing a procedure of highlighting processing in a case of determining as the WLI mode.

FIG. 8 is a flowchart describing a procedure for the highlighting processing in a case where the mode is determined as the WLI mode in step S122. In step S131, the image highlighting section 16 determines whether or not the bleeding region has been detected in step S123.

In a case where the bleeding region has been detected in step S123, the image highlighting section 16 performs the highlighting processing on the bleeding region in the display image based on an amber signal in step S132. Specifically, the image highlighting section 16 combines the amber signal in a pixel belonging to the bleeding region in the display image with the G-channel of the pixel by a first predetermined ratio. In the WLI mode, since the green signal has been allocated to the G-channel of the display image, a signal obtained by combining the amber signal with the green signal by the first predetermined ratio is allocated to the G-channel of the display image. Note that the green signal and the amber signal are image signals corresponding to green light and amber light, respectively. Taking the amber signal for example, the amber signal is an image signal obtained by imaging performed at the time of emission of the amber light in a case of a frame sequential method, and is an image signal of the R-channel, out of image signals obtained by imaging at the time of emission of the amber light in a case of a simultaneous method.

When step S132 ends, or in a case where the bleeding region has not been detected in step S123, step S13 ends. Note that various modifications can be made to step S132, and these modifications will be described later.

Figure 9:
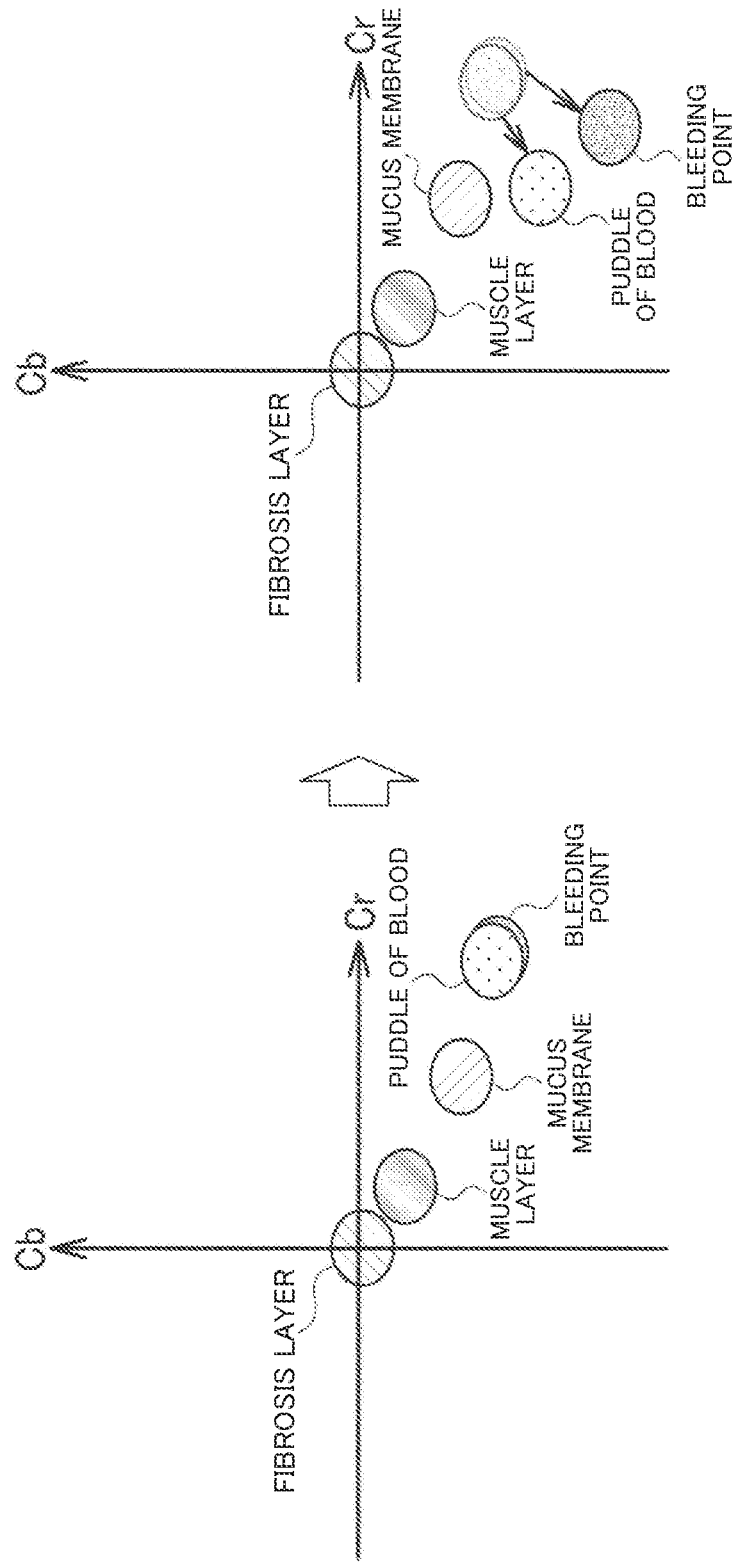
FIG. 9 is a diagram for explaining the highlighting processing in the WLI mode.

FIG. 9 is a diagram describing the highlighting processing in the WLI mode. FIG. 9 illustrates distribution of colors of the object on the CrCb plane. A left drawing in FIG. 9 illustrates distribution before the highlighting processing, and a right drawing illustrates distribution after the highlighting processing.

Before the highlighting processing, since a Cr value of the puddle of blood and that of the bleeding point are both saturated, the puddle of blood and the bleeding point are not separated on the CrCb plane. As a result of combination of the amber signal with the G-channel by the highlighting processing, a hue of the puddle of bleed and that of the bleeding point are rotated counterclockwise on the CrCb plane. In addition, the chroma of the puddle of blood becomes lower than that of the bleeding point. This processing separates the puddle of blood and the bleeding point from each other on the CrCb plane, and thus facilitates visual recognition of the bleeding point in the highlighted display image.

While the amber light is absorbed by hemoglobin as illustrated in FIG. 3, a hemoglobin absorption coefficient HAC of the amber light is relatively lower than that of the green light or the like. Since the green light or the like having a high hemoglobin absorption coefficient HAC is mostly absorbed in the bleeding region, there is little information of variations in concentration of hemoglobin. In contrast, the amber light having a relatively low hemoglobin absorption coefficient HAC holds information of variations in concentration of hemoglobin as gradation also in the bleeding region having a high hemoglobin concentration. Combining the information of variations in concentration of hemoglobin with the G-channel separates the puddle of blood having a relatively low hemoglobin concentration in the bleeding region and the bleeding point having a relatively high hemoglobin concentration in the bleeding region from each other on the CrCb plane.

Figure 10:
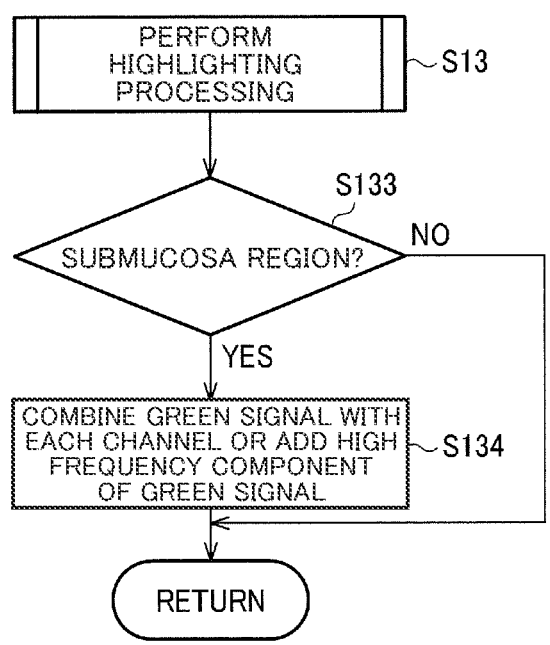
FIG. 10 is a flowchart describing a procedure of highlighting processing in a case of determining as the DRI mode.

FIG. 10 is a flowchart describing a procedure for the highlighting processing in a case where the mode is determined as the DRI mode in step S122. In step S133, the image highlighting section 16 determines whether or not the submucosa region has been detected in step S124.

In a case where the submucosa region has been detected in step S124, the image highlighting section 16 performs the highlighting processing on the submucosa region in the display image based on the green signal in step S134. Specifically, the image highlighting section 16 combines the green signal in a pixel belonging to the submucosa region in the display image with the G-channel of the pixel by a second predetermined ratio. The second predetermined ratio may be different from the first predetermined ratio. In the DRI mode, since the amber signal has been allocated to the G-channel of the display image, a signal obtained by combining the green signal with the amber signal by the second predetermined ratio is allocated to the G-channel of the display image. Note that the green signal is an image signal corresponding to the green light LG illustrated in FIG. 2 or the green light LG2 illustrated in FIG. 3.

When step S134 ends or in a case where the submucosa region has not been detected in step S124, step S13 ends. Note that various modifications can be made to step S134, and these modifications will be described later.

Figure 11:
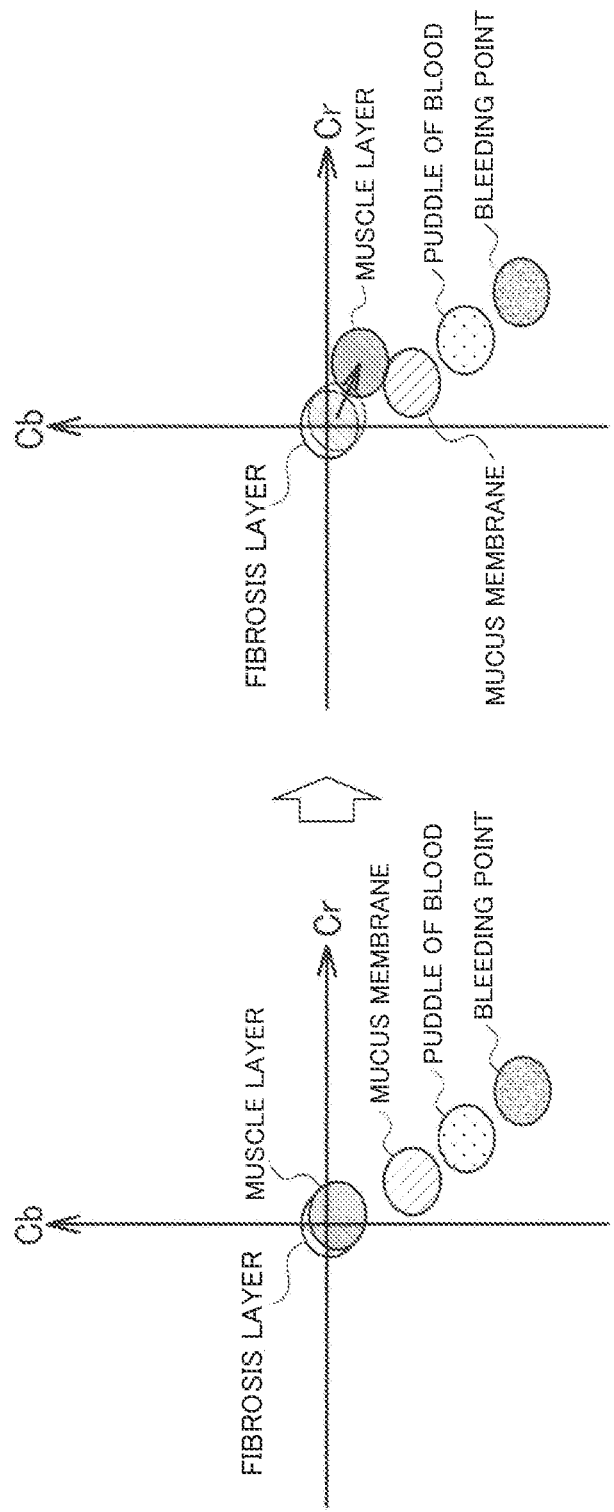
FIG. 11 is a diagram for explaining the highlighting processing in the DRI mode.

FIG. 11 is a diagram describing the highlighting processing in the DRI mode. FIG. 11 illustrates distribution of colors of the object on the CrCb plane. A left drawing in FIG. 11 illustrates distribution before the highlighting processing, and a right drawing illustrates distribution after the highlighting processing.

Since each of the chroma of the fibrosis layer and that of the muscle layer is low before the highlighting processing, the fibrosis layer and the muscle layer are not separated on the CrCb plane. As described above, the submucosa region serving as a target for the highlighting processing includes the submucosa, the fibrosis layer, and the muscle layer. Combining the green signal with the G-channel by the highlighting processing hardly changes the chroma of the fibrosis layer, while increasing the chroma of the muscle layer. At this time, the hue of the muscle layer belongs to the fourth quadrant of the CrCb plane. This processing separates the fibrosis layer and the muscle layer from each other on the CrCb plane, and thus facilitates visual recognition of the boundary between the fibrosis layer and the muscle layer in the highlighted display image. The green light has the high hemoglobin absorption coefficient HAC as illustrated in FIG. 3, and thus has high sensitivity to variations in concentration of hemoglobin. Hence, the green signal holds the information of variations in concentration of hemoglobin contained in tissues as gradation. Since the muscle layer contains a larger amount of hemoglobin than the fibrosis layer does, the green signal in the muscle layer is lower than that in the fibrosis layer. Combining the green signal with the G-channel increases reddishness in the muscle layer as compared with the fibrosis layer. This processing separates the fibrosis layer and the muscle layer from each other on the CrCb plane.

Note that a target region for the highlighting processing is not limited to only the region of the specified object, which is the bleeding region or the submucosa region, and may be a region including the specified object. That is, the target region may be a region that includes a region determined as the specified object in the display image, and that is wider than the region determined as the specified object.

The above-mentioned endoscope apparatus 100 in accordance with the present embodiment includes the light source section 20, the imaging section 30, and the processing section 13. The light source section 20 sequentially or simultaneously emits at least first light and second light as illumination light. The imaging section 30 captures an image using return light from the object irradiated with illumination light, and thereby outputs an image signal. The processing section 13 generates a display image based on the image signal, and outputs the display image to a display device. The first light is the amber light LA in FIG. 3 in the present embodiment. The second light is light belonging to the blue region or the green region, and is the green light LG or the blue light LB in FIG. 2, or the green light LG2 in FIG. 3, in the present embodiment. The image signal includes a first image signal corresponding to the first light, and a second image signal corresponding to the second light. The processing section 13 determines whether or not the specified object is included in an image based on the image signal. In a case of determining that the specified object is included in the image, the processing section 13 then performs color conversion processing or luminance conversion processing on an image region including the specified object using the first image signal or the second image signal to perform the highlighting processing of the specified object, and outputs the highlighted image as the display image.

Since the amber light LA has a hemoglobin absorption coefficient HAC that is smaller than that, of the green light or the like, the information of variations in concentration of hemoglobin can be acquired in a region having a high hemoglobin concentration. In contrast, the blue light or the green light has a large hemoglobin absorption coefficient HAC, the information of variations in concentration of hemoglobin can be acquired in a region having a low hemoglobin concentration. Performing the highlighting processing using image signals acquired by these types of light enables highlighting of the specified object. That is, in the WLI mode in which the object is difficult to be identified in the region having the high hemoglobin concentration, the usage of the amber light enables highlighting of variations in concentration of hemoglobin in the region having the high hemoglobin concentration. In the DRI mode in which the object is difficult to be identified in the region having the low hemoglobin concentration, on the other hand, the usage of the blue light or the green light enables highlighting of variations in concentration of hemoglobin in the region having the low hemoglobin concentration.

Additionally, in the present embodiment, the specified object is the submucosa region. The processing section 13 allocates the first image signal to the G-channel of the display image. The first image signal is the amber signal. This corresponds to the DRI mode in the present embodiment.

Allocating the amber signal to the G-channel of the display image enables display of variations in concentration of hemoglobin in the region having the high hemoglobin concentration such as the puddle of blood. This enables display of a difference in hemoglobin concentration as gradation in a region including a mixture of blood and delivered water, a region around the bleeding point, and the like.

In the present embodiment, in a case of determining that the submucosa region is included in the image, the processing section 13 performs conversion processing that increases a combination ratio of the second image signal to the first image signal in an image region including the submucosa region, and allocates the combined image signal to the G-channel. That is, the processing section 13 increases a ratio of an image signal that accounts for a smaller share of the G-channel of the display image, out of the first image signal based on the first light or the second image signal based on the second light, in the image region including the submucosa region. Note that the second image signal is the blue signal or the green signal.

Note that "increasing the combination ratio of the second image signal to the first image signal" means that making a combination ratio in the target region for highlighting higher than a combination ratio in a region other than the target for highlighting. Note that this includes a case where only the first image signal is allocated to the G-channel in the region other than the target for highlighting.

Since the amber light is allocated to the G-channel in the DRI mode, the boundary between the fibrosis layer and the muscle layer is hard to be identified. The present embodiment combines the blue signal or the green signal with the G-channel, thereby combining the information of variations in concentration of hemoglobin with the G-channel in the fibrosis layer and the muscle layer each having a relatively low hemoglobin concentration. This increases viewability of the fibrosis layer and the muscle layer in the DRI mode.

As described later, in a case of determining that the submucosa region is included in the image, the processing section 13 may combine a high frequency component of the second image signal with the G-channel in the image region including the submucosa region.

The blue signal or the green signal includes texture information of the object. In the present embodiment, combining a high frequency component of the blue signal or the green signal with the G-channel enables highlighting of texture information of the submucosa region. Since the fibrosis layer includes an abundance of texture information as compared with the muscle layer, the viewability of the fibrosis layer and the muscle layer is increased.

As described later, the processing section 13 may determine a region having an indigocarmine concentration that is higher than a predetermined value based on at least one of a hue or chroma. The processing section 13 may increase a combination ratio of the high frequency component of the second image signal in the region determined to have the indigocarmine concentration that is higher than the predetermined value. Note that the meaning of "increasing the combination ratio" is as described above.

As described with reference to FIG. 4, indigocarmine is injected below the early cancer serving as a resection target in the ESD. While the processing section 13 detects the submucosa region from the display image, it can determine the region determined to have the indigocarmine concentration that is higher than the predetermined value out of the submucosa region as the submucosa region serving as the resection target. Increasing a degree of highlighting of the texture information in such a submucosa region enables the viewability of the fibrosis layer and the muscle layer in the submucosa region serving as the resection target.

As described later, in a case of determining that the submucosa region is included in the image, the processing section 13 may perform conversion processing that changes at least one of a hue or chroma in accordance with a signal value of the second image signal in the image region including the submucosa region. That is, the processing section 13 makes a change amount of a hue in a pixel having a larger signal value of the second image signal larger, or makes chroma in the pixel having the larger signal value of the second image signal higher.

The blue signal or the green signal includes the information of variations in concentration of hemoglobin in the fibrosis layer and the muscle layer. Converting a hue or chroma in accordance with the variations in concentration can differentiate between colors or chroma of the fibrosis layer and colors or chroma of the muscle layer. This can increase viewability of the fibrosis layer and the muscle layer.

The processing section 13 may determine the region having the indigocarmine concentration that is higher than the predetermined value as the submucosa region, based on at least one of a hue or chroma. Specifically, the processing section 13 determines that a region having a hue belonging to the blue region as the submucosa region, or determines a region having a hue belonging to the bole region and chroma that is higher than a predetermined value as the submucosa region.

As described with reference to FIG. 4, indigocarmine is injected below the early cancer serving as the resection target in the ESD. The present embodiment can determine a region in which the indigocarmine concentration becomes a value higher than the predetermined value due to the injection of indigocarmine as the submucosa region. For example, a submucosa in which no indigocarmine is injected is not determined as the submucosa region, and only a submucosa in which indigocarmine is injected can be determined as the submucosa region.

In addition, the processing section 13 may determine a region having a hemoglobin concentration that is lower than a predetermined value as the submucosa region, based on at least one of a hue or chroma. Specifically, the processing section 13 determines that a region having a hue belonging to the red region and chroma that is lower than a predetermined value as the submucosa region, or determines a region having chroma that is lower than the predetermined value as the submucosa region.

The submucosa, the fibrosis layer, and the muscle layer that are included in the submucosa region contain a smaller amount of hemoglobin than that contained in the puddle of blood or the like. In accordance with the present embodiment, determining the region having the hemoglobin concentration that is lower than the predetermined value in the display image enables determination of the submucosa region in the display image.

In the present embodiment, the specified object is the bleeding region. The second light is light belonging to the green region. The processing section 13 allocates the second image signal to the G-channel of the display image. This corresponds to the WLI mode in the present embodiment. In the WLI mode, the second light is the green light LG illustrated in FIG. 2.

By allocating the green signal to the G-channel of the display image, the present embodiment displays variations in concentration of hemoglobin in the region having the low hemoglobin concentration, such as the submucosa, the fibrosis layer, and the muscle layer. This differentiates between a hue of the fibrosis layer and that of the muscle layer, thereby enabling visual recognition of the fibrosis layer and the muscle layer.

In the present embodiment, in a case of determining that the bleeding region is included in the image, the processing section 13 performs conversion processing that increases a combination ratio of the first image signal to the second image signal in an image region including the bleeding region, and allocates the combined image signal to the G-channel. Note that the meaning of "increasing the combination ratio" is as described above.

Since the green light is allocated to the G-channel in the WLI mode, the bleeding point is hard to be visually recognized in the puddle of blood. The present embodiment combines the amber signal with the G-channel, thereby combining the information of variations in concentration of hemoglobin to the G-channel in the puddle of blood having the high hemoglobin concentration. This increases viewability of the bleeding point in the puddle of blood in the WLI mode.

As described later, in a case of determining that the bleeding region is included in the image, the processing section 13 may perform conversion processing that changes at least one of a hue or chroma in accordance with a signal value of the first image signal in the image region including the bleeding region. That is, the processing section 13 makes a change amount of a hue in a pixel having a smaller signal value of the first image signal larger, or makes chroma in the pixel having the smaller signal value of the second image signal higher.

The amber signal includes the information of variations in concentration of hemoglobin in the puddle of blood and the bleeding point. Converting a hue or chroma in accordance with the variations in concentration can differentiate between colors or chroma of the puddle of blood and colors or chroma of the bleeding point. This can increase viewability of the bleeding point in the puddle of blood.

In addition, the processing section 13 may determine a region having a hemoglobin concentration that is higher than a predetermined value as the bleeding region, based on at least one of a hue or chroma. Specifically, the processing section 13 determines that a region having a hue belonging to the red region and chroma that is higher than a predetermined value as the bleeding region, or determines a region having chroma that is higher than the predetermined value as the bleeding region.

The bleeding region contains a larger amount of hemoglobin than that contained in tissues of the submucosa or the like. In accordance with the present embodiment, determining a region having a hemoglobin concentration that is higher than a predetermined value in the display image enables determination of the bleeding region in the display image.

In the present embodiment, the processing section 13 changes a determination condition for determining whether or not the specified object is included in the image depending on whether the first image signal is allocated to the G-channel of the display image or the second image signal is allocated to the G-channel of the display image. Specifically, in the DRI mode in which the first image signal is allocated to the G-channel of the display image, the processing section 13 determines whether or not the submucosa region is included in the image. In contrast, in the WLI mode in which the second image signal is allocated to the G-channel of the display image, the processing section 13 determines whether or not the bleeding region is included in the image. The determination condition in each mode is as described above.

This enables determination of the specified object that is difficult to be identified from the display image in each mode. In a case where there is the specified object in the display image, performing the highlighting processing on the region determined as the specified object can increase viewability of the specified object.

Note that the processing section 13 and the control section 12 in accordance with the present embodiment may be composed of the following hardware. The processing section 13 and the control section 12 may be composed of individual hardware, or may be composed of integrated hardware. The hardware can include at least one of a circuit that processes a digital signal or a circuit that processes an analog signal. For example, the hardware can be composed of one or more circuit devices mounted on a circuit board, or one or more circuit elements. The one or more circuit devices are, for example, integrated circuits (ICs) or the like. The one or more circuit elements are, for example, resistors, capacitors, or the like.

In addition, the processing section 13 and the control section 12 may be implemented by a processor. The processing section 13 and the control section 12 may be composed of individual processors, or may be composed of one processor. That is, the control device 10 in accordance with the present embodiment includes a memory that stores information, and a processor that operates based on the information stored in the memory. The memory may be included in the storage section 11. The information is, for example, a program and various kinds of data. The processor includes hardware. The processor determines whether or not the specified object is included in the image based on an image signal. In a case of determining that the specified object is included in the image, the processor performs color conversion processing or luminance conversion processing on an image region including the specified object using the first image signal or the second image signal to perform highlighting processing on the specified object, and outputs the highlighted image as the display image.

The processor may be, for example, a CPU. Note that the processor is not limited to the CPU, but can be any of various kinds of processors such as a graphics processing unit (GPU) and a digital signal processor (DSP). The memory may be a semiconductor memory such as a static random access memory (SRAM) and a dynamic random access memory (DRAM), or may be a register. The memory may be a magnetic storage device such as a hard disk device, or may be an optical storage device such as an optical disk device. For example, the memory stores a computer-readable instruction. Each function of the display image generation section 14, the image determination section 15, the image highlighting section 16, and the control section 12 is implemented as processing when the processor executes the instruction. The instruction may be an instruction set that is included in a program, or may be an instruction that instructs the hardware circuit included in the processor to operate.

Furthermore, the program implementing the processing performed by the processing section 13 in accordance with the present embodiment or the program performed by the processing section 13 and the control section 12 can be stored, for example, in a computer-readable information storage medium. The information storage medium can be implemented by, for example, an optical disk, a memory card, a hard disk drive (HDD), a semiconductor memory, or the like. The semiconductor memory is, for example, a read-only memory (ROM). The processing section 13 and the control section 12 perform various kinds of processing for the present embodiment, based on the program and data stored in the information storage medium. That is, the information storage medium stores the program causing a computer to function as each section of the endoscope apparatus in accordance with the present embodiment. The computer is a device including an input device, a processing section, a storage section, and an output section. The program causes the computer to execute processing of each section. The program is recorded in an information storage medium. As the information storage medium mentioned herein, various kinds of storage media that can be read by an optical detection system, such as an optical disk including a digital versatile disk (DVD) and a compact disk (CD), a magnetic optical disk, a hard disk, a non-volatile memory, and a random-access memory (RAM), can be assumed.

3. Various Kinds of Embodiments

The step S123 and the step S124 in FIG. 7 may be performed both or only one of them.

In step S123 in FIG. 7, the bleeding region may be determined in the following manner in the WLI mode.

The image determination section 15 determines the bleeding region in the display image based on the amber signal. Specifically, the image determination section 15 determines a region having the amber signal whose signal value is smaller than a predetermined value as the bleeding region in the display image. Since the signal value of the amber signal is small in the region having a high degree of absorption of hemoglobin, the image determination section 16 can determine a region having a high hemoglobin concentration as the bleeding region.

In addition, the image determination section 15 may normalize the amber signal with the red signal and determine a region having the normalized amber signal whose signal value is smaller than a predetermined value as the bleeding region. The red signal is an image signal obtained by the red light LR illustrated in FIG. 2 or the red light LR2 illustrated in FIG. 3.

Alternatively, the image determination section 15 may determine a logical OR of a region having a hue belonging to a predetermined hue range and having chroma that is higher than a first predetermined value and a region having the amber signal that is lower than a predetermined value as the bleeding region.

Still alternatively, the image determination section 15 may determine a logical AND of the region having a hue belonging to the predetermined hue range and having chroma that is higher than the first predetermined value and the region having the amber signal whose signal value is smaller than the predetermined value as the bleeding region.

In step S132 in FIG. 8, the highlighting processing may be performed in the bleeding region in the WLI mode as follows.

The image highlighting section 16 combines the amber signal in a pixel belonging to the bleeding region in the display image with the R-channel or B-channel of the pixel by a predetermined ratio.

Alternatively, the image highlighting section 16 may combine the amber signal in a pixel belonging to the bleeding region in the display image with two or more channels of the RGB channels of the pixel by a predetermined ratio.

Still alternatively, the image highlighting section 16 may control hue conversion of the bleeding region using a signal value of the amber signal, instead of adding the amber signal to the display image. Specifically, in a pixel belonging to the bleeding region in the display image, the image highlighting section 16 makes a change amount of a hue larger as a signal value of the amber signal becomes smaller. Since the bleeding point has a signal value of the amber signal that is smaller than that in the puddle of blood, a hue change in the bleeding point becomes large, and it becomes easy to visually recognize the bleeding point.

In addition, the image highlighting section 16 may normalize the amber signal with the red signal and make a change amount of the hue larger as a signal value of the normalized amber signal becomes smaller. Since the red light has low sensitivity to hemoglobin, influence of an object shape and light distribution is dominant in the red signal. Normalizing the amber signal with the red signal enables reduction of the influence of the object shape and light distribution.

In step S124 in FIG. 7, the submucosa region may be determined in the DRI mode as follows.

Figure 12:
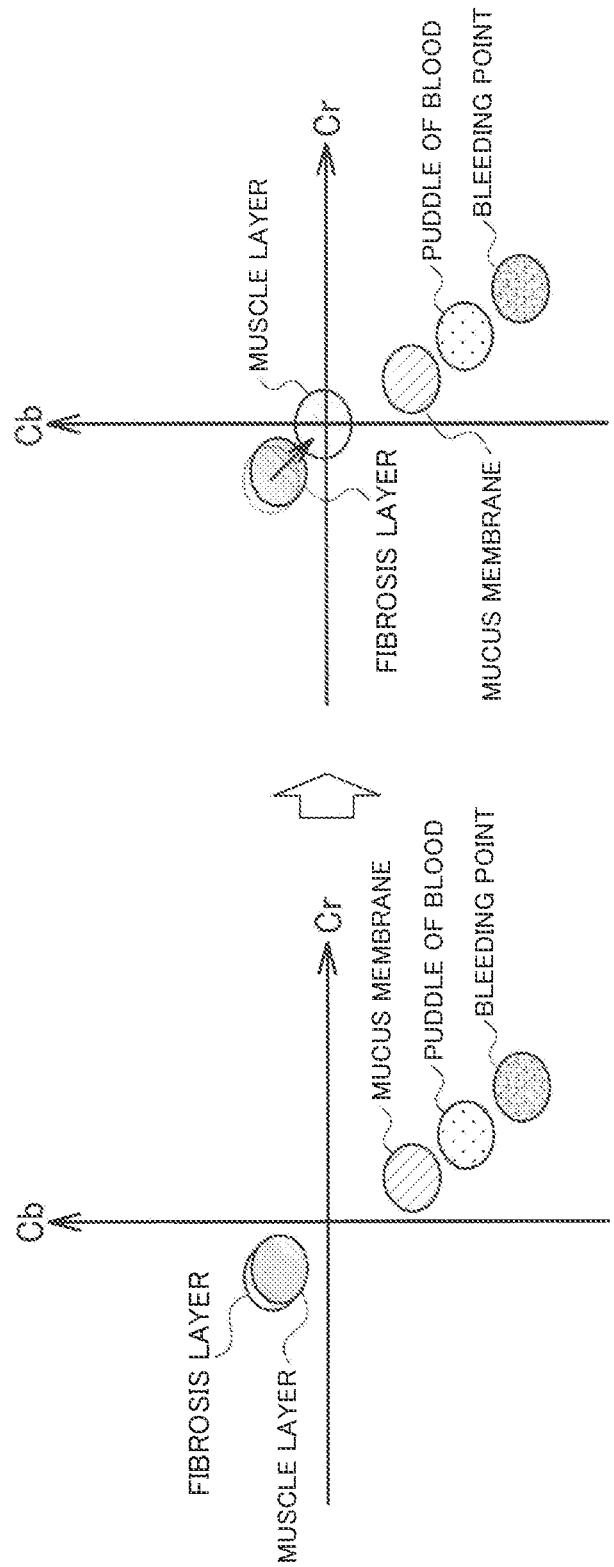
FIG. 12 is a diagram for explaining a modification of the highlighting processing in the DRI mode.

The image determination section 15 may determine a region having a hue belonging to a predetermined range in the display image as the submucosa region. The predetermined hue range belongs to the blue region, and is, for example, a second quadrant of the CrCb plane. In a case where indigocarmine is injected into the submucosa in S1 in FIG. 4, the muscle layer, the submucosa, and the fibrosis layer are dyed with the indigocarmine. As illustrated in a left drawing of FIG. 12, in the DRI image, the fibrosis layer and the muscle layer that have been dyed with the indigocarmine are positioned in the second quadrant of the CrCb plane, and appear to be bluish.

Alternatively, the image determination section 15 may determine a logical OR of a region having chroma that is lower than a second predetermined value and a region having a hue belonging to a predetermined range as the submucosa region.

In step S134 in FIG. 10, the highlighting processing may be performed on the submucosa region in the DRI mode as follows.

The image highlighting section 16 combines the green signal in a pixel belonging to the submucosa region in the display image with the R-channel or B-channel of the pixel by a predetermined ratio.

Alternatively, the image highlighting section 16 may combine the green signal in a pixel belonging to the submucosa region in the display image with two or more channels of the RGB channels of the pixel by a predetermined ratio.

Still alternatively, the image highlighting section 16 may increase a combination ratio of the green signal to each channel in a region determined as belonging to the blue region in the display image. That is, the image highlighting section 16 may make a combination ratio in a region determined as belonging to the blue region higher than a combination ratio in a region determined as not belonging to the blue region. In a case where indigocarmine is injected into the submucosa, the submucosa region is dyed in blue, so that a degree of highlighting of the submucosa region in the dyed region can be increased.

Additionally, the image highlighting section 16 may highlight a structure of the submucosa region based on the green signal. Specifically, the image highlighting section 16 extracts a high frequency component of the green signal, and combines the high frequency component of the green signal in a pixel belonging to the submucosa region of the display image with the G-channel of the pixel. The extraction of the high frequency component is achieved by, for example, a high-pass filter, a bandpass filter, or the like. The fibrosis layer includes an abundance of texture information as compared with the muscle layer, and thus includes a lot of high frequency components. Hence, combining the high frequency component of the green signal can increase viewability of the fibrosis layer.

Alternatively, the image highlighting section 16 may increase a combination ratio of the high frequency component of the green signal to the G-channel in the region determined as belonging to the blue region in the display image. In a case where indigocarmine is injected into the submucosa, the submucosa region is dyed in blue, so that a degree of highlighting of the fibrosis layer in the dyed region can be increased.

Still alternatively, the image highlighting section 16 may combine the high frequency component of the green signal in a pixel belonging to the submucosa region in the display image with the R-channel or B-channel of the pixel. In addition, the image highlighting section 16 may combine the high frequency component of the green signal in a pixel belonging to the submucosa region in the display image with two or more channels of the RGB channels of the pixel.

Although the embodiments to which the present disclosure is applied and the modifications thereof have been described in detail above, the present disclosure is not limited to the embodiments and the modifications thereof, and various modifications and variations in components may be masse in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope apparatus comprising:
a processor including hardware, the processor being configured to:
be connectable to a light source device that sequentially or simultaneously emits at least first light and second light as illumination light and an imaging device that outputs an image signal;
generate a display image based on the image signal; and
output the display image to a display device,
wherein the first light is narrowband light with a peak wavelength between a wavelength at which a hemoglobin absorption coefficient becomes a smallest value and a wavelength at which the hemoglobin absorption coefficient becomes a first maximum value on a short wavelength side of the wavelength at which the hemoglobin absorption coefficient becomes the smallest value,
wherein the second light is light belonging to a blue region or a green region,
wherein the image signal includes a first image signal corresponding to the first light and a second image signal corresponding to the second light, and
wherein the processor is configured to:
determine whether or not a submucosa region is included in an image as a specified object based on the image signal;
in a case where the submucosa region is included in the image as the specified object, perform conversion processing that increases a combination ratio of the second image signal to the first image signal in an image region including the submucosa region, allocate a combined image signal to a G-channel to perform highlighting processing of the specified object, and output an image after the highlighting processing as the display image;
determine whether or not a bleeding region is included in the image as the specified object based on the image signal; and
in a case where the bleeding region is included in the image as the specified object, perform conversion processing that increases a combination ratio of the first image signal to the second image signal in an image region including the bleeding region, allocate the combined image signal to the G-channel to perform highlighting processing of the specified object, and output an image after the highlighting processing as the display image.

2. The endoscope apparatus as defined in claim 1,
wherein in a case of determining that the submucosa region is included in the image as the specified object, the processor is configured to combine a high frequency component of the second image signal to the G-channel in the image region including the submucosa region.

3. The endoscope apparatus as defined in claim 2,
wherein the processor is configured to:
determine a region having an indigocarmine concentration that is higher than a predetermined value based on at least one of a hue or chroma; and
increase a combination ratio of the high frequency component in the region determined as having the indigocarmine concentration that is higher than the predetermined value.

4. The endoscope apparatus as defined in claim 1,
wherein in a case of determining that the submucosa region is included in the image as the specified object, the processor is configured to perform the conversion processing that changes at least one of a hue or chroma in accordance with a signal value of the second image signal in the image region including the submucosa region.

5. The endoscope apparatus as defined in claim 1,
wherein the processor is configured to determine a region having an indigocarmine concentration that is higher than a predetermined value as the submucosa region based on at least one of a hue or chroma.

6. The endoscope apparatus as defined in claim 1,
wherein the processor is configured to determine a region having a hemoglobin concentration that is lower than a predetermined value as the submucosa region based on at least one of a hue or chroma.

7. The endoscope apparatus as defined in claim 1,
in a case of determining that the bleeding region is included in the image as the specified object, the processor is configured to perform the conversion processing that changes at least one of a hue or chroma in accordance with a signal value of the first image signal in the image region including the bleeding region.

8. The endoscope apparatus as defined in claim 1,
wherein the processor is configured to determine a region having a hemoglobin concentration that is higher than a predetermined value as the bleeding region based on at least one of a hue or chroma.

9. The endoscope apparatus as defined in claim 1,
wherein the processor is configured to change a condition of determining whether or not the specified object is included in the image as the specified object depending on whether the first image signal is allocated to a G-channel of the display image or the second image signal is allocated to the G-channel of the display image.

10. The endoscope apparatus as defined in claim 1, further comprising the light source device and the imaging device.

11. An operation method of an endoscope apparatus, the operation method comprising:

sequentially or simultaneously emitting at least first light and second light as illumination light, the first light being narrowband light with a peak wavelength between a wavelength at which a hemoglobin absorption coefficient becomes a smallest value and a wavelength at which the hemoglobin absorption coefficient becomes a first maximum value on a short wavelength side of the wavelength at which the hemoglobin absorption coefficient becomes the smallest value, the second light being light belonging to a blue region or a green region;

capturing an image using return light from an object irradiated with the illumination light to acquire an image signal including a first image signal corresponding to the first light and a second image signal corresponding to the second light;

determining a submucosa region is included in an image as a specified object based on the image signal;

in response to determining that the submucosa region is included in the image as the specified object, performing conversion processing that increases a combination ratio of the second image signal to the first image signal in an image region including the submucosa region, allocating a combined image signal to a G-channel to perform highlighting processing of the specified object, and outputting an image after the highlighting processing as a display image;

determining a bleeding region is included in the image as the specified object based on the image signal; and in response to determining that the bleeding region is included in the image as the specified object, performing conversion processing that increases a combination ratio of the first image signal to the second image signal in an image region including the bleeding region, allocating the combined image signal to the G-channel to perform highlighting processing of the specified object, and outputting an image after the highlighting processing as the display image.

12. A non-transitory information storage medium that stores a program that causes a computer to at least execute:

sequentially or simultaneously emitting at least first light and second light as illumination light, the first light being narrowband light with a peak wavelength between a wavelength at which a hemoglobin absorption coefficient becomes a smallest value and a wavelength at which the hemoglobin absorption coefficient becomes a first maximum value on a short wavelength side of the wavelength at which the hemoglobin absorption coefficient becomes the smallest value, the second light being light belonging to a blue region or a green region;

capturing an image using return light from an object irradiated with the illumination light to acquire an image signal including a first image signal corresponding to the first light and a second image signal corresponding to the second light;

determining whether or not a submucosa region is included in an image as a specified object based on the image signal;

in a case where the submucosa region is included in the image as the specified object, performing conversion processing that increases a combination ratio of the second image signal to the first image signal in an image region including the submucosa region, allocating a combined image signal to a G-channel to perform highlighting processing of the specified object, and outputting an image after the highlighting processing as a display image;

determining whether or not a bleeding region is included in the image as the specified object based on the image signal; and in a case where the bleeding region is included in the image as the specified object, performing conversion processing that increases a combination ratio of the first image signal to the second image signal in an image region including the bleeding region, allocating the combined image signal to the G-channel to perform highlighting processing of the specified object, and outputting an image after the highlighting processing to a display device as the display image.

* * * * *